United States Patent
Ching et al.

(10) Patent No.: US 7,824,875 B2
(45) Date of Patent: *Nov. 2, 2010

(54) **RECOMBINANT ANTIGENS FOR THE DETECTION OF *COXIELLA BURNETII***

(75) Inventors: Wei-Mei Ching, Bethesda, MD (US); Chien-Chung Chao, N. Bethesda, MD (US); Xuan Li, Silver Spring, MD (US); Hua-Wei Chen, Germantown, MD (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 81 days.

This patent is subject to a terminal disclaimer.

(21) Appl. No.: 12/001,599

(22) Filed: Dec. 11, 2007

(65) Prior Publication Data

US 2009/0098647 A1    Apr. 16, 2009

Related U.S. Application Data

(62) Division of application No. 11/401,013, filed on Apr. 4, 2006, now Pat. No. 7,329,503.

(60) Provisional application No. 60/668,591, filed on Apr. 6, 2005.

(51) Int. Cl.
*G01N 33/563*    (2006.01)

(52) U.S. Cl. .................................... 435/7.32

(58) Field of Classification Search ........................ None
See application file for complete search history.

(56) References Cited

PUBLICATIONS

Zhang et al. (Microbiol. Immunol., 42:423-428, 1998).*
SCORE sequence alignment for SEQ ID No. 21, Aug. 21, 2009.*
SCORE sequence alignment for SEQ ID No. 24, Aug. 21, 2009.*
Novagen (Novagen HisTag GSTTag Purification and Detection Tools, 2002).*
Wang et al. (Prot. Express. Purif., 30:140-149, 2003).*
Schweitzer et al. (PNAS, 97:10113-10119, 2000).*
Li et al. (Scand. J. Infect. Dis., 25:569-577, 1993).
Field et al. (J. Infect. Dis., 148:477-487).
Hunt et al. (Infect. Immun. 39:977-981, 1983).
Dupius et al. (J. Clin. Microbiol., 22:484-487, 1985).
Hedrick, Immunity, 21:607-615, 2004.
Bowie et al. (Science, 1990, 247:1306-1310).
Greenspan et al. (Nature Biotechnology 7:936-937, 1999).
Uhaa et al. (J. Clin. Microbiol., 32:1560-1565, 1994).
Abbas et al. (Cellular and Molecular Immunology, 3rd ed., WB Saunders, 1997, see p. 9).
Murray et al. Medical Microbiology, 4th Ed. 2002 see p. 418.

* cited by examiner

*Primary Examiner*—Robert B Mondesi
*Assistant Examiner*—Brian J Gangle
(74) *Attorney, Agent, or Firm*—Joseph K. Hemby, Jr.; Albert M. Churilla; Ning Yang

(57) ABSTRACT

The invention relates to a method for the detection of prior exposure to *Coxiella burnetii* infection by antibody-based assays using recombinant, immunodominant *C. burnetii* polypeptides. The invention also relates to the design of biotin or His-tagged *C. burnetii* proteins useful in the antibody-based assays as standardized antigen reagents.

8 Claims, 3 Drawing Sheets

FIG 1

RECOMBINANT ANTIGENS FOR THE DETECTION OF *COXIELLA BURNETII*

CROSS-REFERENCES TO RELATED APPLICATIONS

This application is a divisional application of application Ser. No. 11/401,013 filed Apr. 4, 2006 now U.S. Pat. No. 7,329,503, issued on Feb. 12, 2008 and claims priority to provisional application No. 60/688,591 filed Apr. 6, 2005.

SEQUENCE LISTING

The application contains a Sequence Listing in paper form. The computer-readable form (CRF) has been previously submitted in the parent application Ser. No. 11/401,013 filed Apr. 4, 2006. In accordance with 37 C.F.R. 1.821(e), please use the CRF filed in the parent application as the CRF for the instant application. I hereby state that the information recorded in computer readable form is identical to the written sequence listing.

BACKGROUND OF THE INVENTION

1. Field of the Invention

The inventive subject matter relates to a method of diagnosing Q fever and detecting exposure to *Coxiella burnetii* using specific immunodominant *C. burnetti* directly as antigen in antibody based assays such as enzyme-linked immunosorbent assays or western blot or the specific immunodominant *C. burnetti* proteins fused to an upstream biotinylated peptide.

2. Description of the Related Art

*Coxiella burnetii* is the causative agent of the disease Q fever and is found worldwide (1,2). The genus *Coxiella* is composed of the single species, *C. burnetii*, short, rod-shaped bacteria, 0.2 to 0.4 μm in diameter and 0.4 to 1.0 μm in length (1, 3). *C. burnetii* is typically maintained as an inapparent infection in domesticated animals, such as cattle, sheep and goats and is found in a number of tick species. The organism persists in feces, urine, milk and tissues so that fomites and infective aerosols are capable of easily forming. Disease occurs among farm workers in close proximity with the animals or their products. Transmission, therefore, is generally by inhalation of infected aerosols or even by the ingestion of raw milk that is infected with the bacteria. Additionally, the organism is highly infectious and is considered a potential biowarfare agent (4).

*C. burnetii* displays an antigenic phase variation, unlike other rickettsial species. In nature, the bacteria expresses phase I antigen, which is a polysaccharide component of the *Coxiella* lipopolysaccharide (5, 6, 7). After passage in culture, the bacteria changes from phase I to phase II. Phase II appears to be a manifestation of deletions of carbohydrate components from the lipopolysaccharide moiety (6).

Clinically, onset of Q fever occurs after an incubation of 18 to 21 days. Although rarely fatal, Q fever is typically abrupt, manifesting with fever, severe headache, chills, severe malaise, myalgia and chest pains. Acute and chronic infection, however, are characterized by different serological profiles (8). Early in the disease progression, Q fever resembles many infections such as influenza, salmonellosis, malaria, hepatitis, and brucellosis. For chronic Q fever, diagnosis is typically demonstrated by antibody against phase I and phase II antigens. In acute infection, diagnosis can typically only be made by direct detection of bacterial antigen or isolation of bacteria since significant serum antibodies are not available at this stage of infection.

Although it is advisable to diagnose Q fever early after infection, early after *C. burnetii* infection diagnosis is difficult due to the difficulty in bacterial isolation and antigen detection and because of the lack of seroconversion at these early stages. Specific complement fixation and agglutinating antibodies are useful in determining infection with agglutination test generally the more sensitive assay method (9-11). Additionally, the binding of fluorescent antibodies such as in indirect fluorescent assays (IFA) or enzyme-linked immunosorbent assays (ELISA) is also helpful in determining *C. burnetii* infection (12). Additional methods, such as direct tissue biopsy, culture of the organism and polymerase chain reaction (PCR) analysis are also useful but are used with much less frequency. The lack of popularity in using biopsy and culture is primarily due to the extensive equipment and expertise requirements as well as the time required to conduct the analysis. PCR offers high sensitivity and the ability to detect bacterial antigen early after infection. However, later in the course of the disease PCR's usefulness is considerably less likely to detect infection than serology (8, 13). Furthermore, PCR is often limited in use based on the availability of trained personnel and equipment.

Central to the development of improved detection and diagnostic immunoassay methods and standardization is the development of more effective antigens for use in existing antibody-based methods. Along these lines, efforts have been made to identify *C. burnetii* immunodominant proteins (14). Accordingly, a number of highly sera-reactive proteins have been identified, including chaperonin, translation elongation factor Tu and the 27 kDa outer membrane protein (Com-1) (14-16). Due to their high reactivity to anti-*C. burnetii* serum, these proteins have been suggested to be valuable antigens in detection and diagnostic assays. However, despite the utililty of immunoassays in the diagnosis of *C. burnetii*, currently available assays suffer from lack of sensitivity and reproducibility. Standardization of antigen will improve assay diagnostic performance and provide early and more accurate treatment regimens (13).

In order to improve standardization of diagnositic assays to *C. burnetii* and to increase assay sensitivity and specificity of detection, other *C. burnetii* immunodominant antigens need to be identified. Improved sensitivity can be achieved by defining antigens expressing a greater number of epitopes well represented in serum antibody repertoires. Alternatively or in addition, methods to ensure attachment of antigen to assay matrixes can be devised with improved orientation of the antigen on the assay matrix with concomitant reduction in steric hinderance in binding of specific anti-*C. burnetii* antibody in patient serum to the antigen.

SUMMARY OF THE INVENTION

Currently available antigenic moieties do not permit highly sensitive and easy to perform methods for the detection of *C. burentii*, the causative agent of the important infectious disease Q fever. Therefore, an object of the invention is the insertion of DNA sequences encoding immunodominant *C. burnetii* proteins into an expression system that when expressed yields a fusion protein composed of a biotinylated peptide and/or a T7-tag upstream of an immunodominant *C. burnetii* protein that can be utilized in antibody based assays for detection or diagnosis of *C. burnetii*. Alternatively, a construct containing a His-tag can also be constructed downstream of the *C. burnetii* insert. This antigen system improves assay standardization by better enabling coupling of measured and predetermined antigen onto solid matrixes for use in antibody-based assays such as ELISA and rapid flow assays. The system also ensures that antigen epitopes are free to bind available antibody.

A further aspect of the invention is the identification of new species of immunodominant C. burnetii proteins and their recombinant forms that are suitable for use as antigen in antibody-based assays.

Another object of the invention is the amplification of assay signal by rolling circle amplification or polymerase chain reaction by the incorporation into the assay secondary antibody containing specific DNA primers.

A still further object of the invention is the use of said recombinant proteins or fusion peptides as vaccine candidates.

BRIEF DESCRIPTION OF THE DRAWINGS

FIG. 1. (a) Map of pET-AB'C. vector. In the figure T7 is the T7 promotor, RBS is the ribosomal binding site. The biotin peptide sequence encodes a 22 amino acid sequence that is selectively biotinylated, catalyzed by the down stream encoded biotin holoenzyme synthetase. FIG (b) shows a map of pET 24a containing a His-tag downstream of the bacterial insert in addition to the upstream T7-tag.

DESCRIPTION OF THE PREFERRED EMBODIMENTS

Figure 2:
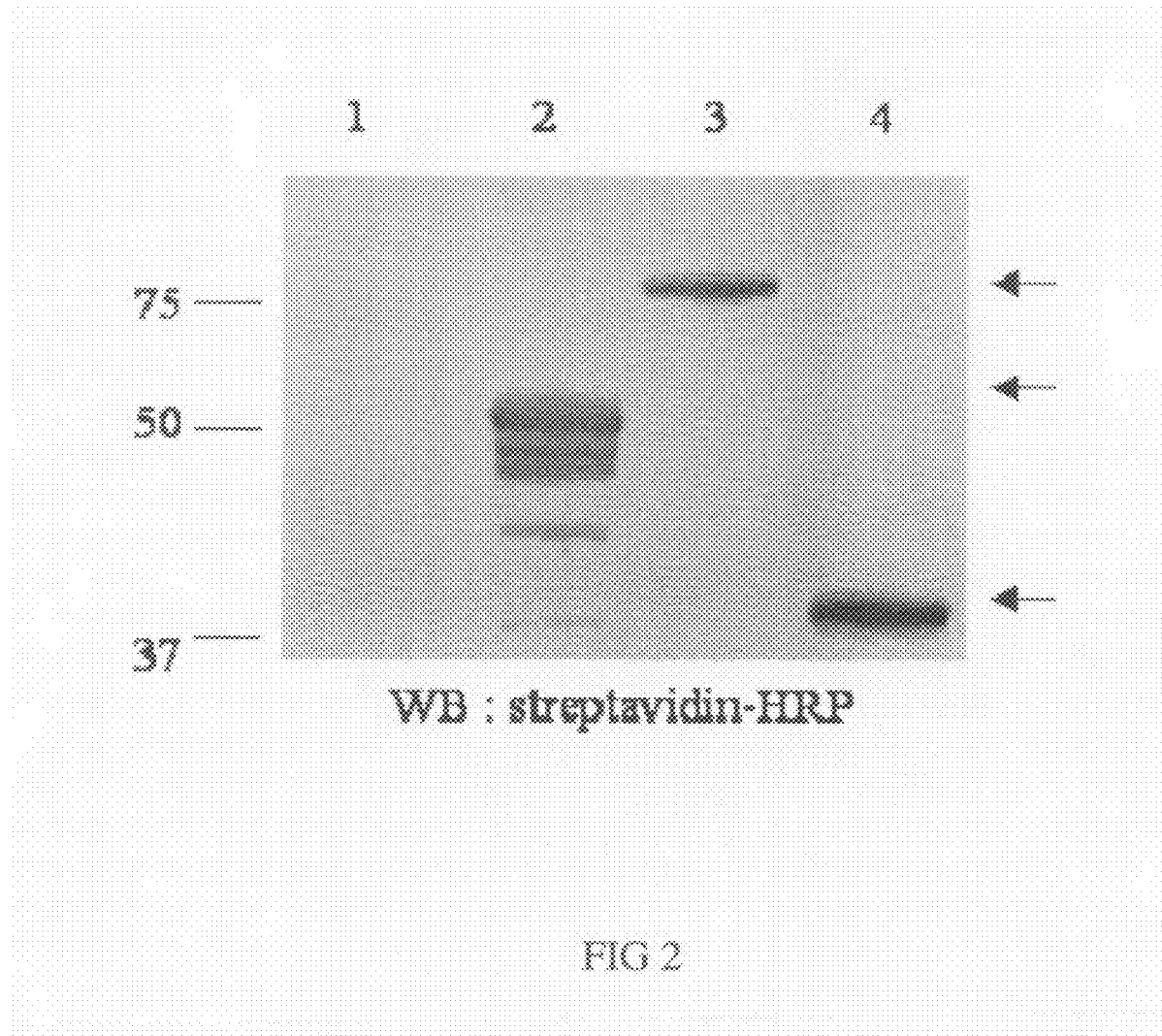
FIG. 2. Western blot of biotinylated C. burnetii recombinant proteins in pET-AB'C. vector. Transferred, separated proteins were exposed to streptavidin-horse radish peroxidase to visualize the biotinylated proteins. Lane 1 shows pET-AB'C. with no insert. Lane 2 shows pET-AB'C. containing FtsZ. Lane 3 is the vector containing chaperonin. Lane 4 is the pET-AB'C. vector containing 27 kDa outer membrane protein (Com-1).

Currently, diagnosis of C. burnetii relies principally on serology based assays such as enzyme-linked immunosorbent assay (ELISA), micro-agglutination, complement fixation and indirect-fluorescent-antibody (IFA) assays with the most commonly employed method being IFA. Although other methods are available, such as polymerase chain reaction, cell culture or immunodetection of antigen in tissue biopsy specimens, these later procedures require considerable infrastructural requirements such as specialized training for personnel, containment facilities and specialized equipment. Furthermore, most of these requirements are beyond the capacity of many health-care facilities. Additionally, many of the serology based assays, because of the lack of standardized antigen, employ a large subjective component in assay interpretation and contain variability from laboratory to laboratory.

Therefore, an aspect of this invention is a method for the detection of prior exposure to C. burnetti, which utilizes as antigen specific recombinantly-produced, C. burentii proteins that are highly sero-reactive, including ompA-like transmembrane domain protein, recA, cell division protein FtsZ, translation elongation factor Tu, chaperonin and 27 kDa outer membrane protein (Com-1). The inventive method contemplates detection of one or more of either ompA-like transmembrane domain protein, recA and cell division protein FtsZ. For greater accuracy and sensitivity, the method can be modified to also include detection of translation elongation factor Tu, chaperonin and 27 kDa outer membrane protein (Com-1).

The inventive method, therefore, by incorporating these specific proteins into an antibody-based assay format is a more accurate and potentially more sensitive assay than other antibody based methods for the detection of C. burnetti. The method, by using standardized antigens, will also enable better analysis of assay data for more definitive determination of prior C. burentii infection and diagnosis.

An additional aspect of this invention is the recombinant expression of immunodominant fusion proteins containing a C. burnetii protein down-stream of a biotin-tagged peptide sequence. The biotin-tagged fusion proteins can be used in antibody-based detection and diagnostic assays for C. burnetii. Application of this invention will result in improved sensitivity of detection of C. burnetii infection with concomitant improvement in diagnosis of Q fever over other diseases presenting with similar symptomotology, especially early after infection. Additionally, inclusion of a biotin tag improves the sensitivity of the assay by enhancing the immobilization of antigen. The biotin tag also improves standardization of the assay since matrixes containing immobilized streptavidin can be produced in high quantities at a uniformly high density with subsequent uniformly high density of streptavidin bound antigen bound via the biotin tag.

Another aspect of this invention is the identification and cloning of C. burnetii proteins that were previously described and sequenced but that were not previously recognized as immunodominant proteins. Therefore, these proteins, recombinantly produced and either used alone or with other C. burnetii recombinant proteins will confer improved standardization and concomitant assay reproducibility and potentially sensitivity in assays for the detection and diagnostic assays for C. burnetii infection and Q fever.

Figure 3:
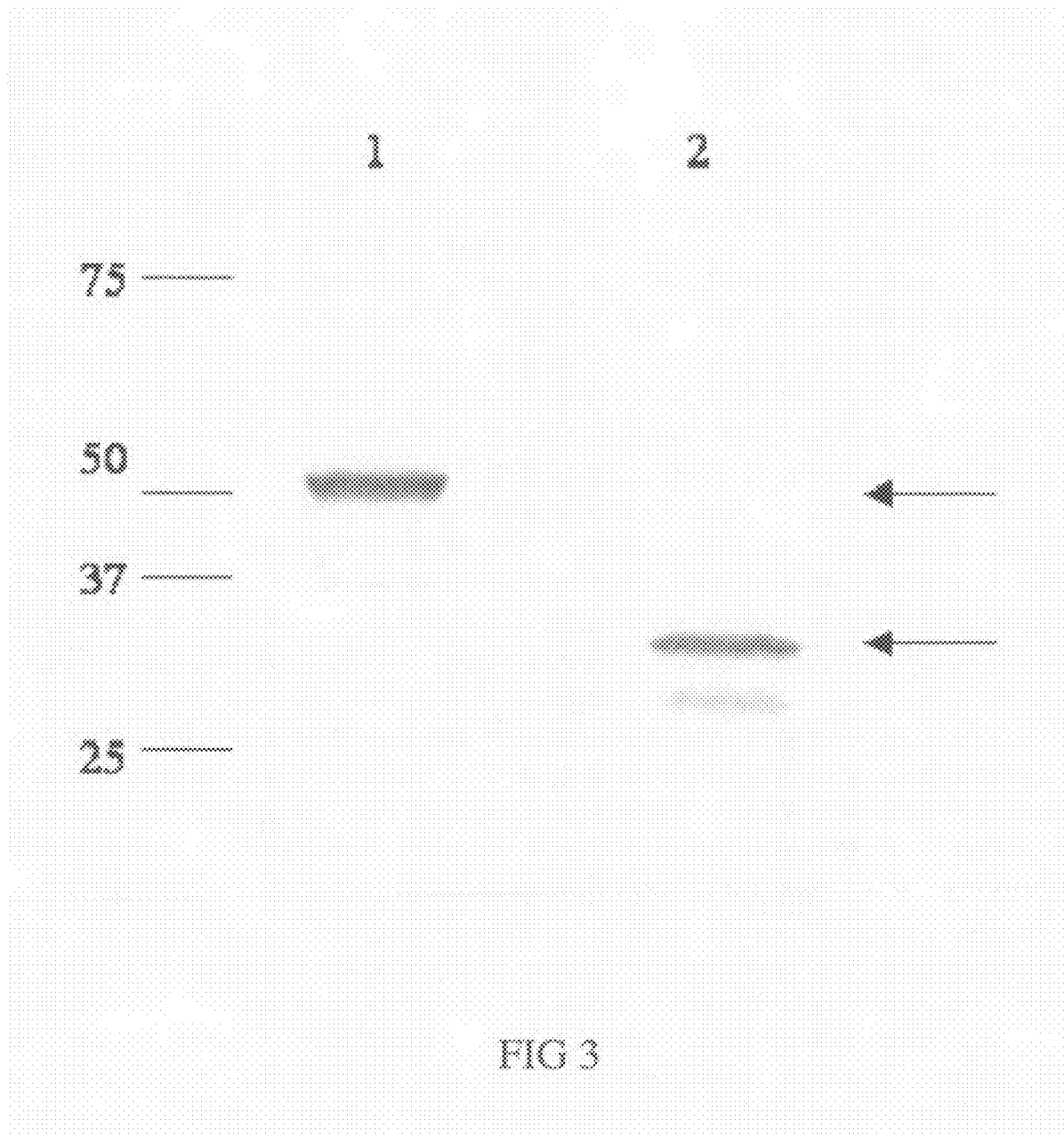
FIG. 3. Western blot of biotinylated C. burnetii recA and ompA-like proteins. Transferred, separated proteins were exposed to streptavidin-horse radish peroxidase to visualize the biotinylated proteins. Lane 1 shows biotinylated recA and Lane 2 shows biotinylated ompA-like protein.

C. burnetii immunodominant proteins were identified and selected by intensity of reactivity to C. burnetii infected patient sera in western blots from 2-dimensional gel electrophoresed C. burnetii proteins. This was accomplished by lysing C. burentii bacteria (Henzeerling strain) and their protein components separated by 2-dimensional (2-D) gel electrophoresis. The 2-D gel separated proteins were then transferred to a polyvinylidene fluoride (PVDF) matrix by western blotting and the immunodominate spots identified by exposing the PVDF to sera from C. burnetii infected patients. The most prominent antigen spots were excised (cut out) from the 2-D gel and subjected to N-terminal amino acid sequence analysis and mass spectrometry (MS) to definitively identify the proteins. Prior to protein identification, the excised 2-D spots were reduced with DTT, alkylated with isoacetamide and subjected to trypsin enzymatic digestion. In order to determine the internal amino acid sequences, the digests were then subjected to further analysis by liquid chromatography (LC) and MS for definitive identification of the digest peptide constituents and ultimately the identity of the protein (FIG. 3).

Western blot studies, as described above, demonstrated a number of proteins that exhibited strong reactivity to anti-C. burnetii serum and therefore were likely candidates for diagnostic assays for Q-fever. Several of these proteins: translation elongation factor Tu, chaperonin and 27 kDa outer membrane protein (Com-1) were previously described to be reactive to C. burnetii serum (12-14). However, three other proteins were identified as also being highly reactive to anti-C. burnetii serum, ompA-like transmembrane domain protein, recA and cell division protein FtsZ. These observations strongly suggest that these other proteins, alone or used together, are valuable as antigens in diagnostic assays.

The following examples illustrate utilization of the *C. burnetii* recombinant peptides in antibody-based detection of *C. burnetii*.

Example 1

Use of *C. burnetii* Peptides as Diagnostic Assay Reagent in ELISA

Currently available diagnostic assays or Q fever primarily rely on serum-based assays for the detection of antibodies to *C. burnetii* with IFA the primary assay method. However, this assay, is often not sensitive and can lead to inaccurate results due to the somewhat subjective nature of the assay procedure. Therefore, other, more objective means of detection of *C. burnetii* infection and diagnosis of Q fever are needed. One such method is enzyme-linked immunosorbent assay (ELISA) or other antibody-based assay. In order to sensitively and reliably diagnosis by this method, suitable, standardized antigen must be available. An aspect of this invention is the use of the recombinant protein antigens in antibody-based assays such as ELISA, lateral flow or immunochromatographic assays.

A number of proteins have been identified in western blot studies as being highly immunoreactive to anti-*C. burnetii* antibody from *C. burnetii* infected patient serum. For example, the proteins translocation elongation factor Tu, 27 kDa outer membrane protein (Com-1) and chaperonin have been previously determined to be reactive to anti-*C. burnetii* serum (12-14). However, based on western blotting of 2D gels, using anti-*C. burnetii* serum, as described above, other proteins have been identified that have equal or greater immunoreactivity. These include cell division protein FtsZ, recA and ompA-like transmembrane domain protein.

Construction of recombinant *C. burnetii* proteins can be carried out by first producing a cDNA copy of the gene sequenced by polymerase chain reaction. The sequence of the amplified DNA of *C. burnetii* ompA-like transmembrane domain protein, rec A and cell division protein FtsZ are shown in SEQ ID No. 13, 14 and 15, respectively and their encoded amino acid sequences as SEQ ID No. 16, 17 and 18, respectively. The DNA sequences *C. burnetii* translation elongation factor Tu, chaperonin and 27 kDa outer membrane protein (Com-1) are represented by SEQ ID No. 19, 20, and 21, respectively and their amino acid sequences shown as SEQ ID No. 22, 23, and 24, respectively. The SEQ ID numbers of the proteins is also summarized in Table 1.

TABLE 1

| | Sequence description |
|---|---|
| SEQ ID No. 1 | cell division protein FtsZ forward primer |
| SEQ ID No. 2 | cell division protein FtsZ reverse primer |
| SEQ ID No. 3 | ompA-like transmembrane domain protein forward primer |
| SEQ ID No. 4 | ompA-like transmembrane domain protein reverse primer |
| SEQ ID No. 5 | rec A forward primer |

TABLE 1-continued

| | Sequence description |
|---|---|
| SEQ ID No. 6 | rec A reverse primer |
| SEQ ID No. 7 | translation elongation factor Tu forward primer |
| SEQ ID No. 8 | translation elongation factor Tu reverse primer |
| SEQ ID No. 9 | chaperonin, 60 kDa forward primer |
| SEQ ID No. 10 | chaperonin, 60 kDa reverse primer |
| SEQ ID No. 11 | 27 kDa outer membrane protein (Com-1) forward primer |
| SEQ ID No. 12 | 27 kDa outer membrane protein (Com-1) reverse primer |
| SEQ ID No. 13 | ompA-like transmembrane domain protein DNA seq. |
| SEQ ID No. 14 | rec A DNA seq. |
| SEQ ID No. 15 | cell division protein FtsZ DNA seq. |
| SEQ ID No. 16 | ompA-like transmembrane domain protein amino acid seq. |
| SEQ ID No. 17 | rec A amino acid seq. |
| SEQ ID No. 18 | cell division protein FtsZ amino acid seq. |
| SEQ ID No. 19 | translation elong. factor Tu DNA seq. |
| SEQ ID No. 20 | chaperonin, 60 kDa DNA seq. |
| SEQ ID No. 21 | 27 kDa outer membrane protein (Com-1) DNA seq. |
| SEQ ID No. 22 | translation elong. factor Tu amino acid seq. |
| SEQ ID No. 23 | chaperonin, 60 kDa amino acid seq. |
| SEQ ID No. 24 | 27 kDa outer membrane protein (Com-1) amino acid seq. |

Expression of the *C. burnetii* protein products can be accomplished by inserting the encoding DNA into a suitable expression system, such as pET 24a. The *C. burnetii* protein can be utilized as an antigen either as an unpurified *E. coli* lysate or purified by any number of methods and subsequently used as antigen in detection or diagnostic assays.

Assays using the recombinantly produced proteins include antibody-based assays such as enzyme-linked immunosorbent assays. As previously mentioned, antigen for the assay can be in the form of unpurified *E. coli* lysate. However, for increased assay sensitivity and reduced background, purified recombinant *C. burnetii* proteins can be used. The preferred method for conducting the assay comprises the following steps:

1. Microtiter plates with 96 wells are coated with 0.3 μg/well of any or all of the recombinant proteins represented by SEQ ID No. 16-18 and/or 22-24 and stored in 4° C. for 2 days.

2. Plates are washed ×3 with wash buffer (0.1% TWEEN®-20 in PBS).
3. Plates are blocked with 200 µl/well of blocking buffer (5% skim milk in wash buffer)×45 minutes and then rinsed three times.
4. Sera is diluted in blocking buffer and 100 µl/well is added and incubated×1 to 2 hours.
5. Plates are washed three times with wash buffer.
6. Plates are then incubated with 100 µl/well of enzyme-labeled (e.g. peroxidase) anti-human immunoglobulin for 1 hour.
7. The plates are washed three times with wash buffer.
8. Substrate is added to the wells and read after 15 to 30 minutes.

A standard curve can be constructed by conducting the above ELISA procedures with the recombinant proteins but utilizing a range of concentrations of specific antibody to *C. burnetii*. The extent of measured binding of patient serum antibody is compared to a graphic representation of the binding of the *C. burnetii*-specific antibody concentrations.

Sensitivity of antibody-based assays, such as ELISA, can be enhanced by substituting the enzyme-substrate step with a molecular detection method. An example of a molecular method employed is the amplification of circular DNA by rolling circle amplification (RCA). In RCA, secondary antibody is conjugated with a single stranded DNA primer comprising the following steps:
  a. 1 mg of sulfo-GMBS powder was added to 4 mg of antibody F(ab')$_2$ in 1 ml, in the dark, for 30 minutes at 37° C., followed by 30 minutes at room temperature;
  b. 2 ml of phosphate buffered saline (PBS) was added to the reaction mixture from a;
  c. the reaction mixture in b, above, was applied unto a pre-equilibrated Presto Desalting Column® (Pierce Biotechnology, Inc, Rockford, Ill.);
  d. the applied material was eluted with PBS and the eluted fractions monitored by absorbance at 280 nm;
  e. pooled fractions containing maleimide-activated antibody was concentrated and stored at 4° C. in the dark until used;
  f. activated DNA was prepared by res-suspending 0.44 mg of thio-DNA (C6 S-S®) (MWG-Biotech Inc, High Point, N.C.) in 150 µl TE buffer with 15 µl of 1 M DTT and incubated at room temperature for 30 minutes;
  g. the DTT was removed from the mixture of step g by applying the mixture to a G-50 micro column and spinning the column at 735×g for 2 minutes;
  h. the activated antibody and activated thio-DNA was then mixed and the mixture incubated in the dark at room temperature for 1 hour then overnight at 4° C.;
  i. product from step h was analyzed by gel electrophoresis.

RCA reactions were undertaken the method comprising the following steps:
  a. mix together on ice 5 nM of primer-conjugated antibody, 10 nM circular DNA, 200 ng of *E. coli*, single-stranded DNA binding protein (SSB), 13 units of T7 SEQUENASE™ and 0.4 mM each of dATP, dCTP, dGTP, 0.3 mM dTTP and 0.1 mM FITC-dUTP in 25 µl of reaction buffer at pH 7.9 containing 20 mM Tris-acetate, 10 mM magnesium acetate, 50 mM potassium acetate and 1 mM DTT;
  b. incubate the mixture of step at 37° C. for up to 30 minutes;
  c. RCA products are then analyzed by measuring fluorescence incorporation of DNA product.

As alternative to RCA, PCR can be utilized using a primer complimentary to the antibody-conjugated DNA, made as described for RCA. Amplification is conducted by utilizing a DNA primer complementary to a template sequence contained on the conjugated DNA.

Example 2

Expression of Tagged Recombinant *C. burnetii* Fusion Proteins

Antigen reactivity to patient serum can be enhanced by either using antigen with increased number of B-cell epitopes, improving efficiency of antigen attachment to the solid matrix prior to serum exposure or by reducing the potential for steric hinderance by improving antigen orientation on the solid matrix.

Previously ELISA methods require direct adhering of assay antigen onto the ELISA plates. Alternatively, antigen can be captured by specific antibody bound to the plates. However, either technique has distinct disadvantages. By adhering antigen directly to plates, potentially reactive epitopes are masked from binding to antibody in test sera. Furthermore, adherence of antigen cannot be completely controlled since the non-specific binding characteristics vary from one lot of plates to another or plate to plate within a lot. Furthermore, non-specific adherence to the plate can vary depending on the conditions used to bind the protein. This variability can be circumvented to a considerable degree by capturing antigen by specific antibody previously adhered to the plates. This suffers, however, by consuming epitopes on the antigen that would normally be available for binding to specific antibody in the test sera. However, another approach to addressing the problem of reproducibly adhering antigen to ELISA plates but still maximally retaining antigen epitopes is to adhere antigen via a biotyin-streptavidin bridge.

Figure 1:
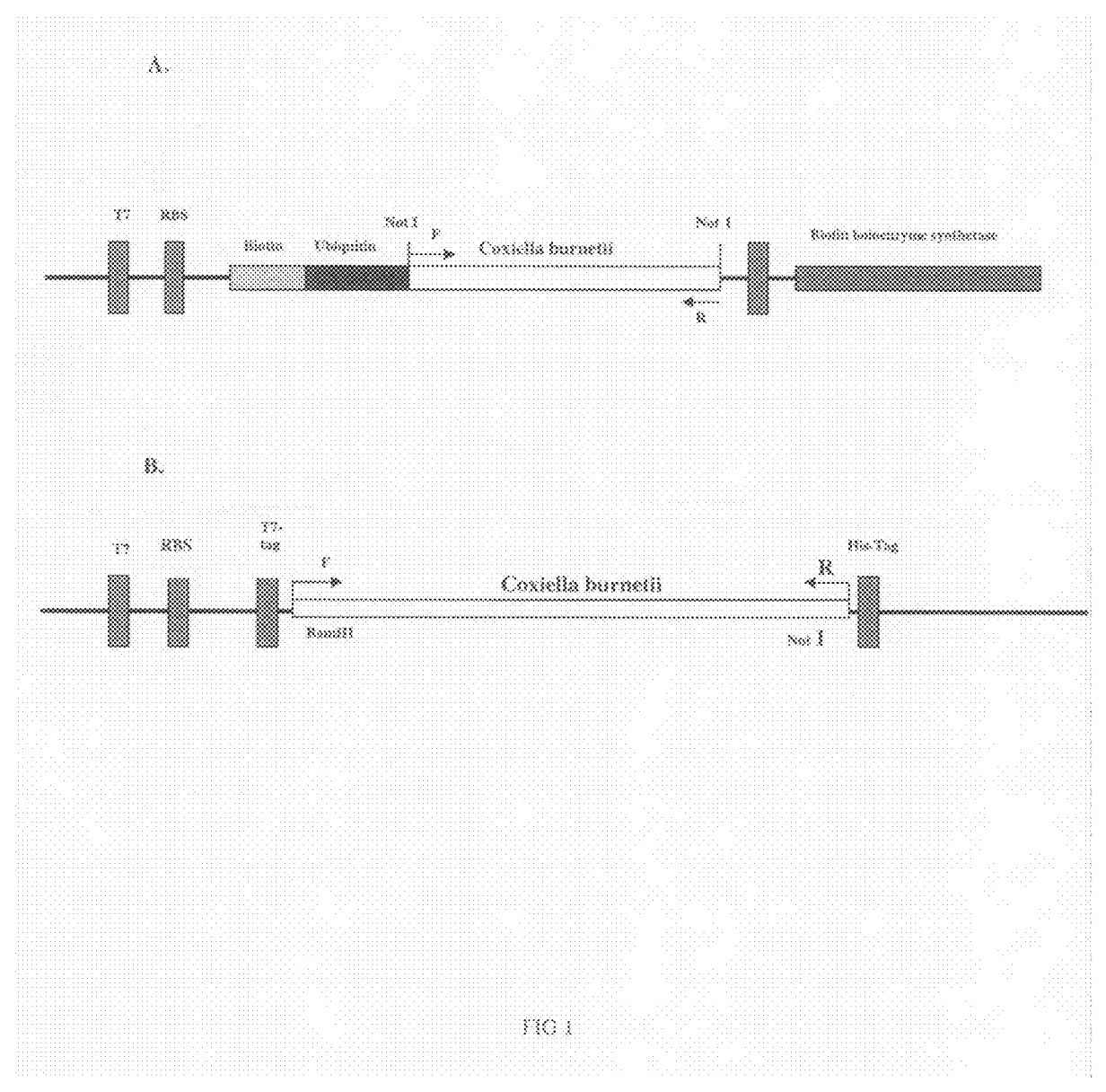

The vector pET-AB'C. vector (17) is used to construct a fusion protein comprising *C. burnetii* antigen containing a biotinylated leader sequence as illustrated in FIG. 1(*a*). Referring to FIG. 1(*a*), biotinylation is catalyzed by biotin holoenzyme synthetase down-stream of the insertion site. The biotinylated fusion antigen is then bound to ELISA plates via strepavidin previously coated onto the plates. This method offers an improvement in assay design by permitting standardization antigen by controlling the amount of strepavidin bound to the plate. Additionally, the method improves the orientation of *C. burnetii* antigen bound to the plate since the antigen will be bound via a biotin attached to streptavidin rather than attached in any number of orientations to the plate itself.

Construction of the pET-AB'C. *C. burnetii* expression vector is carried out by first amplifying DNA encoding the *C. burnetii* proteins translocation elongation factor Tu; ompA-like transmembrane domain protein and; recA, cell division protein FtsZ, chaperonin or 27 kDa outer membrane protein (Com-1) as described in Example 1. The forward and reverse primers used for amplification are SEQ ID No. 1-2 as summarized in Table 1. Amplification with these primers will yield DNA, encoding *C. burnetii* immunodominant proteins, containing Not I enzyme restriction sites. The insertion site on the pET-AB'C. vector is flanked by Not I sites, as well. This permits efficient, site-directed insertion of the sequences into the vector. Any of the *C. burnetii* immunodominant proteins can be inserted and expressed using this vector. FIG. 2 shows the expression of FtsZ, chaperonin and 27 kDa outer membrane protein (Com-1) using the pET-AB'C. expression system.

Once constructed, the recombinant, biotinylated *C. burnetii* antigen can then be bound to ELISA plates that have been pre-coated with streptavidin. The ELISA procedure is then conducted as described in Example 1 from step 2. As previously mentioned, this procedure permits the construction of standardized antigen, in recombinant form that can be reproducibly coupled to ELISA plates. Standardization of antigen coating is also enhanced by prior quality assurance and control of the streptavidin coated ELISA plates to ensure measured amounts of streptavidin are present per well. Furthermore, the sensitivity and reproducibility of assay results are enhanced since the antigen epitopes are conserved for exposure to antibody in patient serum and not bound directly to the plate.

Recombinant *C. burnetii* antigens were also designed such that *C. burnetii* proteins were fused to a His-tag at the C-terminal end and a T7-tag at the opposite end (N-terminal) (FIG. 1(*b*)). As an example, Com-1 or OmpA-like genes were cloned into the pET24a expression vector using the primers SEQ ID No. 25 and 26, for Com-1 forward and reverse primers, respectively and SEQ ID No. 27 and 28 for OmpA forward and reverse primers respectively. The ensuing fusion protein contained an N-terminal T7 tag sequence plus a C-terminal His-tag sequence. Bacteria expressing Com-1 or OmpA-like genes were then grown in Overnight Express Instant TB medium (Novagen (EMD Biosciences, San Diego, Calif.)) with Kanamycin (50 mg/l) at 37° C. for overnight.

Approximately 3 g of bacterial cells (from a 250 ml culture) were then re-suspended in 15 ml lysis solution (BugBuster Master Mix, Novagen (EMD Biosciences, San Diego, Calif.)). The cell suspension was incubated on a rotating mixer at a slow setting for 20 min at room temperature. After centrifugation at 14,000 g for 15 min at 4° C., both Com-1 and OmpA-like fusion proteins were precipitated in the pellets.

The Com-1 pellet was re-suspended in 10 ml of HisBind buffer A (20 mM TrisHCl, pH 8.0, 0.5 M NaCl, and 5 mM imidazole, 8 M urea). Protein sample was applied onto 1 ml Ni-NTA column equilibrated with the same solution except with 10 mM imidazole. After an extensive wash, Com-1 fusion protein was eluted with increased imidazole concentrations (50 mM, 100 mM, and 200 mM). The most pure of the Com-1 fusion fractions were pooled and dialyzed to remove urea against 1×PBS containing 6M, 4M, 2M, 1M, and no urea at 4° C. Refolded Com-1 fusion protein was recovered and stored at −20° C. The refolded pure Com-1 protein was used to raise hyper-immune rabbit sera. The titers were greater than 10e6.

Unlike Com-1 fusion protein, OmpA-like fusion protein was not soluble in 8 M urea. Therefore, the OmpA-like pellet was re-suspended in 20 mM TrisHCl, pH 8.0, 0.5 M NaCl, and 5 mM imidazole 6 M Guanidine Hydrochloride (HisBind buffer B, Novagen). A sample was applied onto 1 ml Ni-NTA column equilibrated with the same buffer. The column was first washed with HisBind buffer B, then washed with buffer A, followed by buffer A except with 10 mM imidazole. After extensive washing, the OmpA-like fusion protein was eluted. The fractions containing Com-1 and OmpA-like fusion proteins that were the most pure were then pooled and dialyzed to remove urea against 1×PBS containing 6M, 4M, 2M, 1M, and no urea at 4° C. OmpA-like fusion protein forms precipitate as urea concentration decreased to 4 M.

REFERENCES

1. Marrie, T. J. 1990. Acute Q fever. In Q Fever, Vol. I. The Disease. T. J. Marrie, Ed.: 125-160. CRC Press. Boca Raton, Fla.
2. Samuel, J. E., M. E. Frazier and L. P. Mallavia. 1985. Correlation of plasmid type and disease caused by *Coxiella burnetii*. Infect. Immun. 49: 775-779.
3. Woldehiwet, Z. 2004. Q fever (coxiellosis): epidemiology and pathogenesis. Res Vet Sci. 77 (2): 93-100.
4. Bellamy, R. J., and A. R. Freedman. 2001. Bioterrorism. QJM 94:227-234.
5. Hackstadt, T. 1986. Antigenic variation in the phase I lipopolysaccharide of *Coxiella burnetii* isolates. Infect. Immun. 52: 337-340.
6. Hackstadt, T., M. G. Peacock, P. J. Hitchcock and R. L. Cole. 1985. Lipopolysaccharide variation in *Coxiella burnetii*: intrastarain heterogeneity in structure and antigenicity. Infect. Immun. 48: 359-365.
7. Brezina, R. 1976. Phase variation phenomenon in *Coxiella burnetii*, p 211-235. In J. Kazar, R. A. Ormsbee, and I. Tarasevitch, (ed.), Rickettsia and Rickettsiales disease. Veda, Bratislava, Slovakia.
8. Maurin, M., and D. Raoult. 1999. Q fever. Clin. Microbiol. Rev. 12: 518-553.
9. Kazar, J., R. Brezina, S. Schramek, A. Palanova, and B. Tvrda. 1981. Suitability of the microagglutination test for detection of post-infection and post vaccination Q fever antibodies in human sera. Acta Virol. 25:235-240.
10. Peter, O., G. Dupuis, W. Burgdorfer, and M. Peacock. 1985. Evaluation of complement fixation and indirect immunofluorescence tests in the early diagnosis of primary Q fever. Eur. J. Clin. Microbiol. 4:394-396.
11. Peter, O., G. Dupuis, M. G. Peacock and W. Burgdorfer. 1987. Comparison of enzyme-linked immunosorbent assay and complement fixatin and indirect fluorescent-antibody tests for detection of *Coxiella burnetii* antibody. J. Clin. Microbiol. 25:1063-1067.
12. Uhaa, I. J., D. B. Fishbein, J. G. Olson, C. C. Rives, D. M. Waag, and J. C. Williams. 1994. Evaluation of specificity of indirect enzyme-linked immunosorbent assay for diagnosis of human Q fever. J. Clin. Microbiol. 32:1560-1565.
13. Fournier, P. E., D. Raoult. 2003. Comparison of PCR and serology assays for early diagnosis of acute Q fever. J. Clin. Microbiol. 41(11): 5094-5098.
14. Zhang, G. K. Kiss, R. Seshadri, L. R. Hendrix, J. E. Samuel. 2004. Identification and cloning of immunodominant antigens of *Coxiella burnetii*. Infect Immun. 72(2): 844-852.
15. Zhang, G. Q., A. Hotta, T. Ho, T. Yamagushi, H. Fukushi and K. Hirai. 1998. Evaluation of a recombinant 27-kDa outer membrane protein of *Coxiella burnetii* as an immunodiagnostic reagent. Microbiol. Immunol. 42:423-428.
16. Zhang, G., H. To, K. E. Russell, L. R. Hendrix, T. Yamaguchi, H. Fukushi, K. Hirai, and J. E. Samuel. 2005. Identification and characterization of an immunodominant 28-kilodalton *Coxiella burnetii* outer membrane protein specific to isolates associated with acute disease. Infec. Immun. 73:1561-1567.
17. Wang, T., E. Evdokimov, K. Yiadom, Z. Yan, P. B. Chock and D. C. H. Yang. 2003. Biotin-ubiquitin tagging of mammalian proteins in *Escherichia coli*. Protein Expression and Purification 30: 140-149.

Having described the invention, one of skill in the art will appreciate in the appended claims that many modifications and variations of the present invention are possible in light of the above teachings. It is therefore, to be understood that, within the scope of the appended claims, the invention may be practices otherwise than as specifically described.

What is claimed is:

1. A method for the detection of *Coxiella burnetii* infection comprising the steps:
   a. Expressing recombinant *Coxiella burnetii* antigens;
   b. exposing said recombinant *Coxiella burnetii* antigens to patient antibody wherein said antigens are selected from the group consisting of ompA-like transmembrane domain protein, recA and cell division protein FtsZ, translation elongation factor Tu, and chaperonin as set forth in SEQ ID NO. 16, 17, 18, 22, and 23, respectively;
   c. detecting binding of said patient antibody to said recombinant antigens.

2. The method of claim 1 wherein the nucleotide sequence encoding said recombinant *Coxiella burnetii* ompA-like transmembrane domain protein, recA, cell division protein FtsZ, translation elongation factor Tu, or chaperonin is set forth in SEQ ID NO:13, 14, 15, 19, or 20, respectively.

3. The method of claim 1, wherein said recombinant *Coxiella burnetii* antigens are immobilized to a matix.

4. The method of claim 3, wherein said recombinant *Coxiella burnetii* antigens are immobilized by a method comprising adding one or more *Coxiella burnetii* antigens to immobilized streptavidin wherein said antigens are included as a component of recombinant fusion polypeptides containing a biotinylated leader sequence fused either directly or via another peptide sequence to the N-terminal end of the complete polypeptide sequence or a fragment of a *Coxiella burnetii* polypeptide which is operatively linked to a biotin holoenzyme synthetase and where said biotinylated leader, *Coxiella burnetii* antigen recombinant fusion polypeptide is immobilized to streptavidin via biotin.

5. The method of claim 3, wherein said recombinant *Coxiella burnetii* antigens are immobilized by a method comprising adding one or more *Coxiella burnetii* antigens to either immobilized anti-T7 or immobilized anti-His antibody wherein said antigen is a component of a recombinant fusion polypeptides containing a T7 tag fused to the N-terminal end of the *Coxiella burnetii* polypeptide which is fused to a His tag at the C-terminal end of said *Coxiella burnetii* polypeptide.

6. The method of claim 4, wherein said *Coxiella burnetii* polypeptide is encoded by all or a fragment of the sequence selected from the group consisting of SEQ ID No. 13, 14, 15, 19, and 20.

7. The of claim 1, wherein sensitivity of detection is enhanced by detecting said binding of said patient antibody by the following additional steps:
   d. exposing said antigen bound patient antibody to a DNA template-conjugated secondary antibody;
   e. amplifying said DNA template by polymerase chain reaction.

8. The method of claim 1, wherein sensitivity of detection is enhanced by detecting said binding of said patient antibody by the following additional steps:
   d. adding DNA primer-conjugated secondary antibody;
   e. amplifying said DNA primer by rolling circle amplification.

* * * * *

SEQUENCE LISTING

<160> NUMBER OF SEQ ID NOS: 28

<210> SEQ ID NO 1
<211> LENGTH: 31
<212> TYPE: DNA
<213> ORGANISM: Coxiella burnetii

<400> SEQUENCE: 1
atctgcggcc gcatgtttga actgggtgaa a                            31

<210> SEQ ID NO 2
<211> LENGTH: 30
<212> TYPE: DNA
<213> ORGANISM: Coxiella burnetii

<400> SEQUENCE: 2
actagcggcc gctcaatctt cctccaggcg                              30

<210> SEQ ID NO 3
<211> LENGTH: 30
<212> TYPE: DNA
<213> ORGANISM: Coxiella burnetii

<400> SEQUENCE: 3
atctgcggcc gcatggctag cgttggtgtc                              30

<210> SEQ ID NO 4
<211> LENGTH: 33
<212> TYPE: DNA
<213> ORGANISM: Coxiella burnetii

<400> SEQUENCE: 4
agtagcggcc gcttacatta agaatttgta gcc                          33

<210> SEQ ID NO 5
<211> LENGTH: 32
<212> TYPE: DNA
<213> ORGANISM: Coxiella burnetii

<400> SEQUENCE: 5
atctgcggcc gcatggataa tcgtagtaat gc                           32

<210> SEQ ID NO 6
<211> LENGTH: 32
<212> TYPE: DNA
<213> ORGANISM: Coxiella burnetii

<400> SEQUENCE: 6
agtagcggcc gctcattctg ctgcattgac tt                           32

<210> SEQ ID NO 7
<211> LENGTH: 34
<212> TYPE: DNA
<213> ORGANISM: Coxiella burnetii

<400> SEQUENCE: 7
atctgcggcc gcatgtcgaa ggaaaaattt gtaa                         34

<210> SEQ ID NO 8
<211> LENGTH: 33
<212> TYPE: DNA
<213> ORGANISM: Coxiella burnetii

```
<400> SEQUENCE: 8
actagcggcc gcttattcaa taatcttcgt tac                          33

<210> SEQ ID NO 9
<211> LENGTH: 34
<212> TYPE: DNA
<213> ORGANISM: Coxiella burnetii

<400> SEQUENCE: 9
actagcggcc gcatggctgc aaaagtttta aaat                         34

<210> SEQ ID NO 10
<211> LENGTH: 30
<212> TYPE: DNA
<213> ORGANISM: Coxiella burnetii

<400> SEQUENCE: 10
agtagcggcc gcttacatca tgccgcccat                              30

<210> SEQ ID NO 11
<211> LENGTH: 31
<212> TYPE: DNA
<213> ORGANISM: Coxiella burnetii

<400> SEQUENCE: 11
atcagcggcc gcgtgaagaa ccgtttgact g                            31

<210> SEQ ID NO 12
<211> LENGTH: 31
<212> TYPE: DNA
<213> ORGANISM: Coxiella burnetii

<400> SEQUENCE: 12
agtagcggcc gcttactttt ctacccggtc g                            31

<210> SEQ ID NO 13
<211> LENGTH: 657
<212> TYPE: DNA
<213> ORGANISM: Coxiella burnetii

<400> SEQUENCE: 13
atggctagcg ttggtgtcac ttccgctgca ttggcgggtg gtcctgatta tgtacctgct    60
cccagctacg cgggcgttta tcttgaaggt aacttgggtt atgcataccg tccgtggcgg   120
aaggatgcaa ccactgttgt aggtctcgcg aaacaagcta gactttttagg aagttcttct   180 cgaggcaacg gtggctttac tttcggtgcg atctcggtt atcaatttaa ccagtacttc   240
gccgttgaag gcggttggtt ctatctgcct aaagtgaaat tcacaaccac tggcgttgta   300
aatggacttg cggcaggaac atacacagtt aaaagcggga tggcttacgc tgcattgaaa   360
gggatggcgc tgtttatga aaacacttat gttttcggga attaggcgt tgcttacacc   420 tacaatcgag ctaacgccgg tctgccgact aataaaattc cggcaacctt cggttcacgt   480
tccagatttt ggaacccgct gtttgccgcc ggtgttcagt actacttcac acctaactgg   540
tctgtgaatg ctcagtacac gttcgtaccg ggctatcgaa atgcttcatc taagcgtttt   600
gtagcgccag ttacccatct gttcaccgta ggccttggct acaaattctt aatgtaa      657

<210> SEQ ID NO 14
<211> LENGTH: 1032
<212> TYPE: DNA
```

<213> ORGANISM: Coxiella burnetii

<400> SEQUENCE: 14

```
atggataatc gtagtaatgc gctgaatgct gctttgtcgc aaattgaacg tcagttcggt      60
aaaggttcgg tcatgcgttt gggtgatccc ggactcatac cggacatcga tgtcatttca     120
acaggctcct tgggtcttga tatcgctttg ggtgtgggtg gattacccccg cggtcggatc    180
attgaaattt acgggccgga agcttccgga aaaaccacgc tagccttaca aacgatcgct     240
tcttgtcagc gtatgggcgg tacggctgct tttgtggatg cggaacatgc gttggatgcc     300
atttatgcgg gcaaattagg cgttaaagta gaggacttgt tggtatccca gccggataca     360
ggggaacaag ctttagaaat tacagacatg ttggttcgct cgggcgctgt tgatctgatc     420
gtgatcgact ccgttgccgc cctgacgcca aagccgaaa ttgaaggtga tatgggcgat      480
tctcatatgg gtttgcaagc gcgtttaatg tcacaagcgc tgcgcaagct cacggcaaac    540
attaagaaat ccaataccct tagtgatatt attaatcaaa tacgtatgaa atcggcgtt     600
atgtttggta atccggaaac gaccaccgga gggaacgcgc ttaagttta ttcgtcagta     660
cgcttggata ttcgccgcat cggagcgatc aaaaagggcg aagagatttt aggcagtgaa    720
actcgagtaa aggtagttaa aaacaaggtg gcgccgcctt tccgtcaagt cgagtttgat    780
attctttacg gtcttggtat ttcgcgtgaa agtgagttaa ttgacctcgg tgttaaaaat    840
gaactggtcg aaaaagcagg cgcttggtac agttacaatg gcgagcgtat cggccaaggg    900
aaagaaaacg ttcgacaatt tttccttgaa aatccaaaaa ttgcagggga aattgaaaca    960
cgtttgcgtg aaaaactgtt gccgcatcgg caaggcgaga aatcgctga agaagtcaat    1020
gcagcagaat ga                                                       1032
```

<210> SEQ ID NO 15
<211> LENGTH: 1161
<212> TYPE: DNA
<213> ORGANISM: Coxiella burnetii

<400> SEQUENCE: 15

```
atgtttgaac tgggtgaaac ctcaccgcaa atgcccaaa taaaagtcat cggcatcggc       60
ggtggtggcg gaaacgctat cgagcatatg atcgctgaga atatcgatgg tgtagagttt    120
gtttgtgcga ataccgattc tcaagcctta gggcgatcta atgcgcgggt cgttttacag    180
ctcggtgatg aaatcaccaa agggcttggg gcgggtgctg atcccagcgt cggtcgtcaa    240
gcggctgaag aggcgcgcga tcgcattcgt gaaattctcg aaggaacaga catggttttc    300
ctaaccgcgg gtatgggcgg gggcacggga actggcgctg caccgatttt cgcggaagtc    360
gctaaagagt tgggtatttt gaccgtcgcc gttgtgacga agccattcgt atttgaaggt    420
aaaaaacgga tggatgtggc ggaagaagga atcaaggcgc taggtaacta tgtggattca    480
ttgatcacca tcccccaataa taaattactg aatgtgctgg gcaaaaacat aaccctttta    540
aatgctttta aagcagcgaa taatgtctta ttaggcgccg ttcaagggat tgccgatttg    600
attactcgtc ctggattgat aaacgtcgat tttgccgatg tacgcaccgt catgtcagaa    660
atgggaatgg ctatgatggg aactggcgtt agcagcggcg aaaacagagc tcgcgaagcc    720
gcggaagccg ctatcgcaag ccctctgttg aagacgtgca atttcacggg cgctcgaggc    780
gtgttagtca atatcactgc tgggatggat ttatcgattg gcgagttcga acaggtcggc    840
gaagctgtga aggcattgc ttctgaaaca gcgacggtcg tcatcggtac cgttatcgat    900
cccgatatga gcgatgaact gcgcgtgacg gtggtggtga caggattggg ttcgcacgcc    960
```

-continued

```
ggtggcggcg ctggtgttcc cttaaaacct gtaaaaaaca cgaaaaacga tggcacatta    1020
gattaccatc aattggatcg gccgacttat atgcgaaatc aagaaccgtc taaacgcacg    1080
gtagatctcg aagaacaacg cgaccgggat tttgaatatt tagatattcc cgcgttttta    1140
cgtcgcctgg aggaagattg a                                              1161
```

<210> SEQ ID NO 16
<211> LENGTH: 231
<212> TYPE: PRT
<213> ORGANISM: Coxiella burnetii

<400> SEQUENCE: 16

```
Met Ser Val Lys Lys Leu Val Thr Leu Ala Thr Leu Thr Met Ala Ser
1               5                   10                  15

Val Gly Val Thr Ser Ala Ala Leu Ala Gly Gly Pro Asp Tyr Val Pro
            20                  25                  30

Ala Pro Ser Tyr Ala Gly Val Tyr Leu Glu Gly Asn Leu Gly Tyr Ala
        35                  40                  45

Tyr Arg Pro Trp Arg Lys Asp Ala Thr Thr Val Val Gly Leu Ala Lys
    50                  55                  60

Gln Ala Arg Leu Leu Gly Ser Ser Arg Gly Asn Gly Gly Phe Thr
65                  70                  75                  80

Phe Gly Ala Asp Leu Gly Tyr Gln Phe Asn Gln Tyr Phe Ala Val Glu
                85                  90                  95

Gly Gly Trp Phe Tyr Leu Pro Lys Val Lys Phe Thr Thr Thr Gly Val
            100                 105                 110

Val Asn Gly Leu Ala Ala Gly Thr Tyr Thr Val Lys Ser Gly Met Ala
        115                 120                 125

Tyr Ala Ala Leu Lys Gly Met Ala Pro Val Tyr Glu Asn Thr Tyr Val
    130                 135                 140

Phe Gly Lys Leu Gly Val Ala Tyr Thr Tyr Asn Arg Ala Asn Ala Gly
145                 150                 155                 160

Leu Pro Thr Asn Lys Ile Pro Ala Thr Phe Gly Ser Arg Ser Arg Phe
                165                 170                 175

Trp Asn Pro Leu Phe Ala Ala Gly Val Gln Tyr Tyr Phe Thr Pro Asn
            180                 185                 190

Trp Ser Val Asn Ala Gln Tyr Thr Phe Val Pro Gly Tyr Arg Asn Ala
        195                 200                 205

Ser Ser Lys Arg Phe Val Ala Pro Val Thr His Leu Phe Thr Val Gly
    210                 215                 220

Leu Gly Tyr Lys Phe Leu Met
225                 230
```

<210> SEQ ID NO 17
<211> LENGTH: 343
<212> TYPE: PRT
<213> ORGANISM: Coxiella burnetii

<400> SEQUENCE: 17

```
Met Asp Asn Arg Ser Asn Ala Leu Asn Ala Ala Leu Ser Gln Ile Glu
1               5                   10                  15

Arg Gln Phe Gly Lys Gly Ser Val Met Arg Leu Gly Asp Pro Gly Leu
            20                  25                  30

Ile Pro Asp Ile Asp Val Ile Ser Thr Gly Ser Leu Gly Leu Asp Ile
        35                  40                  45
```

Ala Leu Gly Val Gly Gly Leu Pro Arg Gly Arg Ile Ile Glu Ile Tyr
        50                  55                  60

Gly Pro Glu Ala Ser Gly Lys Thr Thr Leu Ala Leu Gln Thr Ile Ala
 65                  70                  75                  80

Ser Cys Gln Arg Met Gly Gly Thr Ala Ala Phe Val Asp Ala Glu His
                85                  90                  95

Ala Leu Asp Ala Ile Tyr Ala Gly Lys Leu Gly Val Lys Val Glu Asp
                100                 105                 110

Leu Leu Val Ser Gln Pro Asp Thr Gly Glu Gln Ala Leu Glu Ile Thr
                115                 120                 125

Asp Met Leu Val Arg Ser Gly Ala Val Asp Leu Ile Val Ile Asp Ser
        130                 135                 140

Val Ala Ala Leu Thr Pro Lys Ala Glu Ile Glu Gly Asp Met Gly Asp
145                 150                 155                 160

Ser His Met Gly Leu Gln Ala Arg Leu Met Ser Gln Ala Leu Arg Lys
                165                 170                 175

Leu Thr Ala Asn Ile Lys Lys Ser Asn Thr Leu Val Ile Phe Ile Asn
                180                 185                 190

Gln Ile Arg Met Lys Ile Gly Val Met Phe Gly Asn Pro Glu Thr Thr
        195                 200                 205

Thr Gly Gly Asn Ala Leu Lys Phe Tyr Ser Ser Val Arg Leu Asp Ile
        210                 215                 220

Arg Arg Ile Gly Ala Ile Lys Lys Gly Glu Glu Ile Leu Gly Ser Glu
225                 230                 235                 240

Thr Arg Val Lys Val Val Lys Asn Lys Val Ala Pro Pro Phe Arg Gln
                245                 250                 255

Val Glu Phe Asp Ile Leu Tyr Gly Leu Gly Ile Ser Arg Glu Ser Glu
                260                 265                 270

Leu Ile Asp Leu Gly Val Lys Asn Glu Leu Val Glu Lys Ala Gly Ala
        275                 280                 285

Trp Tyr Ser Tyr Asn Gly Glu Arg Ile Gly Gln Gly Lys Glu Asn Val
        290                 295                 300

Arg Gln Phe Phe Leu Glu Asn Pro Lys Ile Ala Gly Glu Ile Glu Thr
305                 310                 315                 320

Arg Leu Arg Glu Lys Leu Leu Pro His Arg Gln Gly Lys Ile Ala
                325                 330                 335

Glu Glu Val Asn Ala Ala Glu
                340

<210> SEQ ID NO 18
<211> LENGTH: 386
<212> TYPE: PRT
<213> ORGANISM: Coxiella burnetii

<400> SEQUENCE: 18

Met Phe Glu Leu Gly Glu Thr Ser Pro Gln Asn Ala Gln Ile Lys Val
1               5                   10                  15

Ile Gly Ile Gly Gly Gly Gly Asn Ala Ile Glu His Met Ile Ala
                20                  25                  30

Glu Asn Ile Asp Gly Val Glu Phe Val Cys Ala Asn Thr Asp Ser Gln
            35                  40                  45

Ala Leu Gly Arg Ser Asn Ala Arg Val Val Leu Gln Leu Gly Asp Glu
        50                  55                  60

Ile Thr Lys Gly Leu Gly Ala Gly Ala Asp Pro Ser Val Gly Arg Gln
65                  70                  75                  80

```
Ala Ala Glu Glu Ala Arg Asp Arg Ile Arg Glu Ile Leu Gly Thr
                85                  90                  95

Asp Met Val Phe Leu Thr Ala Gly Met Gly Gly Gly Thr Gly Thr Gly
            100                 105                 110

Ala Ala Pro Ile Phe Ala Glu Val Ala Lys Glu Leu Gly Ile Leu Thr
            115                 120                 125

Val Ala Val Val Thr Lys Pro Phe Val Phe Glu Gly Lys Lys Arg Met
        130                 135                 140

Asp Val Ala Glu Glu Gly Ile Lys Ala Leu Gly Asn Tyr Val Asp Ser
145                 150                 155                 160

Leu Ile Thr Ile Pro Asn Asn Lys Leu Leu Asn Val Leu Gly Lys Asn
                165                 170                 175

Ile Thr Leu Leu Asn Ala Phe Lys Ala Ala Asn Val Leu Leu Gly
                180                 185                 190

Ala Val Gln Gly Ile Ala Asp Leu Ile Thr Arg Pro Gly Leu Ile Asn
            195                 200                 205

Val Asp Phe Ala Asp Val Arg Thr Val Met Ser Glu Met Gly Met Ala
210                 215                 220

Met Met Gly Thr Gly Val Ser Ser Gly Glu Asn Arg Ala Arg Glu Ala
225                 230                 235                 240

Ala Glu Ala Ala Ile Ala Ser Pro Leu Leu Gly Asp Val Asp Phe Thr
                245                 250                 255

Gly Ala Arg Gly Val Leu Val Asn Ile Thr Ala Gly Met Asp Leu Ser
            260                 265                 270

Ile Gly Glu Phe Glu Gln Val Gly Glu Ala Val Lys Ala Phe Ala Ser
        275                 280                 285

Glu Thr Ala Thr Val Val Ile Gly Thr Val Ile Asp Pro Asp Met Ser
        290                 295                 300

Asp Glu Leu Arg Val Thr Val Val Thr Gly Leu Gly Ser His Ala
305                 310                 315                 320

Gly Gly Gly Ala Gly Val Pro Leu Lys Pro Val Lys Asn Thr Lys Asn
                325                 330                 335

Asp Gly Thr Leu Asp Tyr His Gln Leu Asp Arg Pro Thr Tyr Met Arg
            340                 345                 350

Asn Gln Glu Pro Ser Lys Arg Thr Val Asp Leu Glu Glu Gln Arg Asp
        355                 360                 365

Arg Asp Phe Glu Tyr Leu Asp Ile Pro Ala Phe Leu Arg Arg Leu Glu
    370                 375                 380

Glu Asp
385

<210> SEQ ID NO 19
<211> LENGTH: 1194
<212> TYPE: DNA
<213> ORGANISM: Coxiella burnetii

<400> SEQUENCE: 19
atgtcgaagg aaaaatttgt aagagagaag ccgcacgtga acgtgggtac gattggtcac      60
gtggatcatg ggaagacgac gttaacggcg gcattgacga aggtgttgtc ggagaaatac     120
ggcggagaaa agaaagcctt tgaccagatt gacaacgcgc cggaagagcg cgcgcgaggg     180
atcacgatag cgacgtcgca cgtggaatac caaagcgaca agcgccacta cgcgcacgta     240
gactgcccag gccacgcgga ttatgtgaag aacatgatca cgggagcggc gcaaatggac     300
```

-continued

| | |
|---|---|
| ggagcgatat tggtggtgag cgcagcggac ggcccgatgc cgcaaacgcg ggaacacatt | 360 |
| gtattggcga agcaagtggg tgttccgaac atagtggttt acttgaacaa agcggacatg | 420 |
| gtggatgaca aagagctgtt ggaattagtg gaaatggaag tgagggattt attgaacagt | 480 |
| tatgatttcc ctggggatga gacgccgata atagtggggt cagcgttaaa ggcgttagaa | 540 |
| ggtgacaaga gtgaggttgg ggagccatcg ataatcaaat tagtgaaaac gatggacacg | 600 |
| tacttcccgc agccggagcg agcgatagac aaaccgtttt taatgccgat cgaagatgtg | 660 |
| ttttcgatat cgggccgagg gacggtggtg acgggacgcg tagagcgagg gatcatcaaa | 720 |
| gtgggcgacg agatagagat tgtggggatc aaggacacga cgaagacgac gtgcacgggc | 780 |
| gttgagatgt tcgcaaatt attggatgaa ggtcaagcgg gtgacaacgt aggaatttta | 840 |
| ttgagaggga cgaaacgcga agaagtggag cgtggtcaag tattggcgaa accgggatcg | 900 |
| atcacgccac acaagaaatt tgaggcggag atttatgtgt tgtcgaagga agaaggggga | 960 |
| cgccacacac cgttttaca aggctatcga ccgcaatttt atttccgcac gacggacgtg | 1020 |
| acgggccagt tattgagttt accggagggg atagagatgg tgatgccggg agataacgtg | 1080 |
| aaagtgacgg ttgaattgat tgcgccggta gcgatggatg aagggctacg atttgcggta | 1140 |
| cgggaaggtg gccgcacggt gggcgccgga gtggtaacga agattattga ataa | 1194 |

<210> SEQ ID NO 20
<211> LENGTH: 1659
<212> TYPE: DNA
<213> ORGANISM: Coxiella burnetii
<400> SEQUENCE: 20

| | |
|---|---|
| atggctgcaa aagttttaaa attttcccac gaggtattac acgcaatgag tcgtggcgtg | 60 |
| gaagttttgg ccaacgcggt aaaagtgacg ttgggaccaa aaggtcgcaa tgtcgtttta | 120 |
| gataaatcat ttggcgcacc aaccattact aaagacggcg ttagcgtagc taaagaaatc | 180 |
| gagttggaag acaaatttga aaatatgggc gctcaaatgg ttaaagaagt ggcttcgcgt | 240 |
| acatcagacg atgcgggtga tggtaccaca acagcgaccg tactggctca agcgattttg | 300 |
| gttgaaggca tcaaagccgt tattgctgga atgaacccca tggatttgaa acggggtatt | 360 |
| gataaagccg taacggcagc ggtagctgaa ttgaagaaaa tttccaagcc ttgcaaagac | 420 |
| cagaaagcga ttgcgcaagt aggcaccatt tctgcgaatt cggataagtc gattggagat | 480 |
| attattgcgg aagcgatgga gaaagtgggc aaagaaggcg tcataacagt agaagatggc | 540 |
| tctggtcttg aaaacgcgct tgaagtagtt gaaggtatgc agttcgatcg tggttacttg | 600 |
| tcgccatact ttatcaacaa tcaacaaaac atgagtgcgg agcttgaaaa tccgtttatc | 660 |
| ttattggttt acaagaagat ttctaatatt cgtgaactca ttccgttgtt agaaaacgta | 720 |
| gcaaagtctg gtcggccctt attggtgatt gccgaagata tcgaaggcga agctttagcg | 780 |
| acgttagtgg ttaataatat tcgcggtgtt gttaaagtcg cggctgtaaa agcacctggc | 840 |
| tttggcgatc gtcgtaaagc gatgttgcaa gatattgctg ttttgacggg cggtaaggtt | 900 |
| atttctgaag aagtcggatt gtcccttgag gccgcttctt tggatgattt aggttctgct | 960 |
| aaacgcgttg ttgtcactaa agatgacacc accatcattg atggttctgg tgacgccggt | 1020 |
| gacattaaaa accgcgtgga gcaaatccga aaagaaatag aaaatagctc gtcggactat | 1080 |
| gataaagaga aattacaaga acgtctggca aaattagccg gtggtgtggc ggtcattaaa | 1140 |
| gtgggcgctc cgactgaagt tgaaatgaaa gagaaaaaag cccgcgtgga agatgcctta | 1200 |
| catgcgacgc gcgcagccgt cgaagaaggt gtcgtaccgg gtggtggcgt tgctttaatc | 1260 |

```
cgcgtgctta aatcgcttga ttcagtggaa gttgagaatg aagaccaacg cgtgggcgtg    1320
gaaattgctc gccgtgcgat ggcttacccg ctttctcaaa tcgtgaaaaa cacgggtgtt    1380
caagcagccg ttgtcgctga caaagtcttg aaccataaag acgttaatta tggttataac    1440
gcagcgacgg gtgaatacgg tgacatgatt gagatgggta ttctcgaccc aaccaaagtg    1500
acccgcaccg cgttgcaaaa cgcagcttct atcgctggtc ttatgattac caccgaatgt    1560
atggtaacag aagctcccaa gaagaaagag gagtcgatgc ccggcggcgg tgacatgggc    1620
ggcatgggag gaatgggcgg catgggcggc atgatgtaa                          1659
```

<210> SEQ ID NO 21
<211> LENGTH: 759
<212> TYPE: DNA
<213> ORGANISM: Coxiella burnetii

<400> SEQUENCE: 21

```
gtgaagaacc gtttgactgc actattttta gccggaacct tgaccgcagg cgtggcgata     60 gccgcccccct ctcaattcag ttttctcct caacaagtca agacataca aagcatcgtc    120 caccattatt tagtcaacca cccagaagtt ttagtagaag catcccaagc attgcaaaaa    180
aagacagaag cgcaacaaga gaacacgct caacaagcaa ttaaagaaaa tgcaaagaaa    240
ttatttaacg accctgcatc accagtggca ggcaatcctc atggcaatgt acattggtt    300 gaatttttcg attatcaatg tggccattgc aaagccatga attctgttat tcaagctatc    360
gtgaaacaaa ataaaaacct ccgcgttgtc ttcaaagaac tgcccatttt tggcggccaa    420
tcgcaatacg ctgccaaagt atcattagca gccgctaaac aaggaaaata ttatgctttc    480
cacgacgcgc tgctcagtgt cgacggccaa ttatcagaac aaatcaccct tcaaaccgca    540
gaaaaagtag gattaaatgt tgctcagctc aaaaaagaca tggataatcc tgctatccaa    600
aaacaactgc gtgataactt ccaattagct caatcgttac agctagcagg caccccgacg    660
ttcgtcattg gtaataaagc gttaaccaaa ttcggttta acccggcgc cacctcacaa     720 caaaaccttc aaaagaaat cgaccgggta gaaaagtaa                           759
```

<210> SEQ ID NO 22
<211> LENGTH: 397
<212> TYPE: PRT
<213> ORGANISM: Coxiella burnetii

<400> SEQUENCE: 22

```
Met Ser Lys Glu Lys Phe Val Arg Glu Lys Pro His Val Asn Val Gly
  1               5                  10                  15

Thr Ile Gly His Val Asp His Gly Lys Thr Thr Leu Thr Ala Ala Leu
             20                  25                  30

Thr Lys Val Leu Ser Glu Lys Tyr Gly Gly Glu Lys Lys Ala Phe Asp
         35                  40                  45

Gln Ile Asp Asn Ala Pro Glu Glu Arg Ala Arg Gly Ile Thr Ile Ala
     50                  55                  60

Thr Ser His Val Glu Tyr Gln Ser Asp Lys Arg His Tyr Ala His Val
 65                  70                  75                  80

Asp Cys Pro Gly His Ala Asp Tyr Val Lys Asn Met Ile Thr Gly Ala
                 85                  90                  95

Ala Gln Met Asp Gly Ala Ile Leu Val Val Ser Ala Ala Asp Gly Pro
            100                 105                 110

Met Pro Gln Thr Arg Glu His Ile Val Leu Ala Lys Gln Val Gly Val
```

```
                    115                 120                 125
Pro Asn Ile Val Val Tyr Leu Asn Lys Ala Asp Met Val Asp Lys
    130                 135                 140

Glu Leu Leu Glu Leu Val Glu Met Glu Val Arg Asp Leu Leu Asn Ser
145                 150                 155                 160

Tyr Asp Phe Pro Gly Asp Glu Thr Pro Ile Ile Val Gly Ser Ala Leu
                165                 170                 175

Lys Ala Leu Glu Gly Asp Lys Ser Glu Val Gly Glu Pro Ser Ile Ile
                180                 185                 190

Lys Leu Val Glu Thr Met Asp Thr Tyr Phe Pro Gln Pro Glu Arg Ala
                195                 200                 205

Ile Asp Lys Pro Phe Leu Met Pro Ile Glu Asp Val Phe Ser Ile Ser
    210                 215                 220

Gly Arg Gly Thr Val Val Thr Gly Arg Val Glu Arg Gly Ile Ile Lys
225                 230                 235                 240

Val Gly Asp Glu Ile Glu Ile Val Gly Ile Lys Asp Thr Thr Lys Thr
                245                 250                 255

Thr Cys Thr Gly Val Glu Met Phe Arg Lys Leu Leu Asp Glu Gly Gln
                260                 265                 270

Ala Gly Asp Asn Val Gly Ile Leu Leu Arg Gly Thr Lys Arg Glu Glu
                275                 280                 285

Val Glu Arg Gly Gln Val Leu Ala Lys Pro Gly Ser Ile Thr Pro His
                290                 295                 300

Lys Lys Phe Glu Ala Glu Ile Tyr Val Leu Ser Lys Glu Glu Gly Gly
305                 310                 315                 320

Arg His Thr Pro Phe Leu Gln Gly Tyr Arg Pro Gln Phe Tyr Phe Arg
                325                 330                 335

Thr Thr Asp Val Thr Gly Gln Leu Leu Ser Leu Pro Glu Gly Ile Glu
                340                 345                 350

Met Val Met Pro Gly Asp Asn Val Lys Val Thr Val Glu Leu Ile Ala
                355                 360                 365

Pro Val Ala Met Asp Glu Gly Leu Arg Phe Ala Val Arg Glu Gly Gly
                370                 375                 380

Arg Thr Val Gly Ala Gly Val Val Thr Lys Ile Ile Glu
385                 390                 395

<210> SEQ ID NO 23
<211> LENGTH: 552
<212> TYPE: PRT
<213> ORGANISM: Coxiella burnetii

<400> SEQUENCE: 23

Met Ala Ala Lys Val Leu Lys Phe Ser His Glu Val Leu His Ala Met
1               5                   10                  15

Ser Arg Gly Val Glu Val Leu Ala Asn Ala Val Lys Val Thr Leu Gly
                20                  25                  30

Pro Lys Gly Arg Asn Val Leu Asp Lys Ser Phe Gly Ala Pro Thr
                35                  40                  45

Ile Thr Lys Asp Gly Val Ser Val Ala Lys Glu Ile Glu Leu Glu Asp
    50                  55                  60

Lys Phe Glu Asn Met Gly Ala Gln Met Val Lys Glu Val Ala Ser Arg
65                  70                  75                  80

Thr Ser Asp Asp Ala Gly Asp Gly Thr Thr Thr Ala Thr Val Leu Ala
                85                  90                  95
```

-continued

```
Gln Ala Ile Leu Val Glu Gly Ile Lys Ala Val Ile Ala Gly Met Asn
            100                 105                 110
Pro Met Asp Leu Lys Arg Gly Ile Asp Lys Ala Val Thr Ala Ala Val
            115                 120                 125
Ala Glu Leu Lys Lys Ile Ser Lys Pro Cys Lys Asp Gln Lys Ala Ile
130                 135                 140
Ala Gln Val Gly Thr Ile Ser Ala Asn Ser Asp Lys Ser Ile Gly Asp
145                 150                 155                 160
Ile Ile Ala Glu Ala Met Glu Lys Val Gly Lys Glu Gly Val Ile Thr
                165                 170                 175
Val Glu Asp Gly Ser Gly Leu Glu Asn Ala Leu Glu Val Val Glu Gly
            180                 185                 190
Met Gln Phe Asp Arg Gly Tyr Leu Ser Pro Tyr Phe Ile Asn Asn Gln
            195                 200                 205
Gln Asn Met Ser Ala Glu Leu Glu Asn Pro Phe Ile Leu Leu Val Asp
            210                 215                 220
Lys Lys Ile Ser Asn Ile Arg Glu Leu Ile Pro Leu Leu Glu Asn Val
225                 230                 235                 240
Ala Lys Ser Gly Arg Pro Leu Leu Val Ile Ala Glu Asp Ile Glu Gly
                245                 250                 255
Glu Ala Leu Ala Thr Leu Val Val Asn Asn Ile Arg Gly Val Val Lys
            260                 265                 270
Val Ala Ala Val Lys Ala Pro Gly Phe Gly Asp Arg Arg Lys Ala Met
            275                 280                 285
Leu Gln Asp Ile Ala Val Leu Thr Gly Gly Lys Val Ile Ser Glu Glu
            290                 295                 300
Val Gly Leu Ser Leu Glu Ala Ala Ser Leu Asp Asp Leu Gly Ser Ala
305                 310                 315                 320
Lys Arg Val Val Val Thr Lys Asp Asp Thr Thr Ile Ile Asp Gly Ser
                325                 330                 335
Gly Asp Ala Gly Asp Ile Lys Asn Arg Val Glu Gln Ile Arg Lys Glu
            340                 345                 350
Ile Glu Asn Ser Ser Ser Asp Tyr Asp Lys Glu Lys Leu Gln Glu Arg
            355                 360                 365
Leu Ala Lys Leu Ala Gly Gly Val Ala Val Ile Lys Val Gly Ala Ala
            370                 375                 380
Thr Glu Val Glu Met Lys Glu Lys Ala Arg Val Glu Asp Ala Leu
385                 390                 395                 400
His Ala Thr Arg Ala Ala Val Glu Glu Gly Val Val Pro Gly Gly Gly
                405                 410                 415
Val Ala Leu Ile Arg Val Leu Lys Ser Leu Asp Ser Val Glu Val Glu
            420                 425                 430
Asn Glu Asp Gln Arg Val Gly Val Glu Ile Ala Arg Arg Ala Met Ala
            435                 440                 445
Tyr Pro Leu Ser Gln Ile Val Lys Asn Thr Gly Val Gln Ala Ala Val
            450                 455                 460
Val Ala Asp Lys Val Leu Asn His Lys Asp Val Asn Tyr Gly Tyr Asn
465                 470                 475                 480
Ala Ala Thr Gly Glu Tyr Gly Asp Met Ile Glu Met Gly Ile Leu Asp
                485                 490                 495
Pro Thr Lys Val Thr Arg Thr Ala Leu Gln Asn Ala Ala Ser Ile Ala
            500                 505                 510
Gly Leu Met Ile Thr Thr Glu Cys Met Val Thr Glu Ala Pro Lys Lys
```

```
                515                 520                 525
Lys Glu Glu Ser Met Pro Gly Gly Asp Met Gly Met Gly Gly
            530                 535                 540

Met Gly Gly Met Gly Gly Met Met
545                 550

<210> SEQ ID NO 24
<211> LENGTH: 252
<212> TYPE: PRT
<213> ORGANISM: Coxiella burnetii

<400> SEQUENCE: 24

Met Lys Asn Arg Leu Thr Ala Leu Phe Leu Ala Gly Thr Leu Thr Ala
1               5                   10                  15

Gly Val Ala Ile Ala Ala Pro Ser Gln Phe Ser Phe Ser Pro Gln Gln
            20                  25                  30

Val Lys Asp Ile Gln Ser Ile Val His His Tyr Leu Val Asn His Pro
        35                  40                  45

Glu Val Leu Val Glu Ala Ser Gln Ala Leu Gln Lys Lys Thr Glu Ala
    50                  55                  60

Gln Gln Glu Glu His Ala Gln Ala Ile Lys Glu Asn Ala Lys Lys
65                  70                  75                  80

Leu Phe Asn Asp Pro Ala Ser Pro Val Ala Gly Asn Pro His Gly Asn
                85                  90                  95

Val Thr Leu Val Glu Phe Phe Asp Tyr Gln Cys Gly His Cys Lys Ala
            100                 105                 110

Met Asn Ser Val Ile Gln Ala Ile Val Lys Gln Asn Lys Asn Leu Arg
        115                 120                 125

Val Val Phe Lys Glu Leu Pro Ile Phe Gly Gly Gln Ser Gln Tyr Ala
    130                 135                 140

Ala Lys Val Ser Leu Ala Ala Ala Lys Gln Gly Lys Tyr Tyr Ala Phe
145                 150                 155                 160

His Asp Ala Leu Leu Ser Val Asp Gly Gln Leu Ser Glu Gln Ile Thr
                165                 170                 175

Leu Gln Thr Ala Glu Lys Val Gly Leu Asn Val Ala Gln Leu Lys Lys
            180                 185                 190

Asp Met Asp Asn Pro Ala Ile Gln Lys Gln Leu Arg Asp Asn Phe Gln
        195                 200                 205

Leu Ala Gln Ser Leu Gln Leu Ala Gly Thr Pro Thr Phe Val Ile Gly
    210                 215                 220

Asn Lys Ala Leu Thr Lys Phe Gly Phe Ile Pro Gly Ala Thr Ser Gln
225                 230                 235                 240

Gln Asn Leu Gln Lys Glu Ile Asp Arg Val Glu Lys
                245                 250

<210> SEQ ID NO 25
<211> LENGTH: 30
<212> TYPE: DNA
<213> ORGANISM: Coxiella burnetii

<400> SEQUENCE: 25
cgggatccgc ccctctctcaa ttcagttttt                                    30

<210> SEQ ID NO 26
<211> LENGTH: 36
<212> TYPE: DNA
<213> ORGANISM: Coxiella burnetii
```

```
<400> SEQUENCE: 26
aagaatgcgg ccgcctttc tacccggtcg atttct                            36

<210> SEQ ID NO 27
<211> LENGTH: 30
<212> TYPE: DNA
<213> ORGANISM: Coxiella burnetii

<400> SEQUENCE: 27
cgggatccgg tggtcctgat tatgtacctg                                  30

<210> SEQ ID NO 28
<211> LENGTH: 37
<212> TYPE: DNA
<213> ORGANISM: Coxiella burnetii

<400> SEQUENCE: 28
aagaatgcgg ccgccattaa gaatttgtag ccaaggc                          37
```